United States Patent
Imai et al.

(10) Patent No.: US 6,171,520 B1
(45) Date of Patent: *Jan. 9, 2001

(54) REAGENTS FOR LABELING SH GROUPS, PROCESS FOR THE PREPARATION OF THEM AND METHOD FOR LABELING WITH THEM

(75) Inventors: Kazuhiro Imai, Tokyo; Hiromichi Eto, Narita; Takeshi Kotsugai, Sawara; Tadashi Narita, Shisui-machi, all of (JP)

(73) Assignee: SS Pharmaceutical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/945,885

(22) PCT Filed: Mar. 14, 1997

(86) PCT No.: PCT/JP97/00821

§ 371 Date: Nov. 14, 1997

§ 102(e) Date: Nov. 14, 1997

(87) PCT Pub. No.: WO97/33884

PCT Pub. Date: Sep. 18, 1997

(30) Foreign Application Priority Data

Mar. 15, 1996 (JP) .................................................. 8-085965
Mar. 15, 1996 (JP) .................................................. 8-085966

(51) Int. Cl.[7] .............. C09K 11/07; C07D 401/12; C07D 401/14; G01N 33/532
(52) U.S. Cl. ............... 252/301.16; 546/102; 546/104
(58) Field of Search .................................... 546/102, 104; 530/387.1; 252/301.16

(56) References Cited

U.S. PATENT DOCUMENTS

| 4,745,181 | 5/1988 | Law ........................................ 530/387 |
| 4,946,958 | * 8/1990 | Campbell ............................... 546/104 |
| 5,688,642 | * 11/1997 | Chrisey ................................... 435/6 |

FOREIGN PATENT DOCUMENTS

| 0 082 636 | 6/1983 | (EP) . |
| 0 216 553 | 1/1987 | (EP) . |
| 0 257 541 | 3/1988 | (EP) . |
| 0 263 657 | 4/1988 | (EP) . |
| 2 233 450 | 1/1991 | (GB) . |
| 63-57572 | 3/1988 | (JP) . |

(List continued on next page.)

OTHER PUBLICATIONS

Machida M et al. Chem. Phar,. Bull. 26(2), 596–604 1978.*
Chemical Abstracts No. 153709, vol. 91, No. (Nov. 5, 1979).
Chemical Abstracts No. 44171, vol. No. 5, (Jul. 31, 1978).
Chemical Abstracts No. 141517, vol. No. 11, (Mar. 17, 1997).

(List continued on next page.)

\* cited by examiner

*Primary Examiner*—Evelyn Mei Huang
(74) *Attorney, Agent, or Firm*—Oblon, Spivak, McClelland, Maier & Neustadt, P.C.

(57) ABSTRACT

Disclosed are SH-labeling reagents containing acridine compounds represented by the following formula (I):

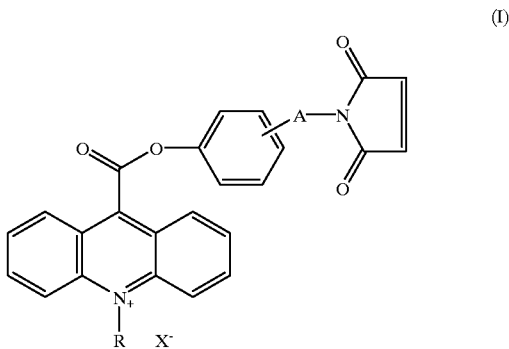

wherein
A represents the following group:

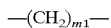

or

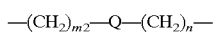

in which Q represents a group —S[+]RX[−]—, a group —N[+]RR$_1$X[−]— wherein R$_1$ represents an alkyl group having 1 to 6 carbon atoms or an aryl group, a group

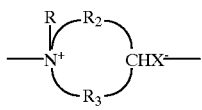

wherein R$_2$ and R$_3$ may be the same or different and are each independently a group —(CH$_2$)$_k$— (k: a number of 1 to 3) or —O(CH$_2$CH$_2$O)$_l$— (l: a number of 1 to 3),
m1 stands for a number of 1 to 6,
m2 denotes a number of 0 to 2,
n means a number of 1 to 2;
R represents an alkyl group having 1 to 6 carbon atoms or an aryl group; and
X[−] represents an anion, or intermediates thereof; preparation processes of the acridine compounds; and methods for labeling analytes by using the compounds.

15 Claims, No Drawings

FOREIGN PATENT DOCUMENTS

| | | |
|---|---|---|
| 63-101368 | 5/1988 | (JP) . |
| 5-255263 | 10/1993 | (JP) . |
| 6-122679 | 5/1994 | (JP) . |
| 6-158039 | 6/1994 | (JP) . |

OTHER PUBLICATIONS

Chemical Abstracts No. 136268, vol. 99, No. 17, (Oct. 24, 1983).

Chemical Abstracts No. 209233, vol. 111, No. 23, (Dec. 4, 1989).

REAGENTS FOR LABELING SH GROUPS, PROCESS FOR THE PREPARATION OF THEM AND METHOD FOR LABELING WITH THEM

This application is the national phase of PCT/JP97/00821, filed on Mar. 14, 1997.

TECHNICAL FIELD

This invention relates to a reagent for labeling SH groups, which makes use of an acridine compound containing a maleimide group. More specifically, the present invention is concerned with an SH-labeling reagent using as a labeling substance an acridine compound, its production process and a labeling method making use of the same. The acridine compound contains therein a maleimide group, which binds to SH groups contained in or easily introducible into an analyte such as an amino acid, a protein or the like, and produces chemiluminescence.

BACKGROUND ART

Acridinium esters, acridine compounds, are useful as chemiluminescent labeling substances for their possession of high efficiencies of luminescence. Use of such an acridinium ester as a chemiluminescent label in an immunoluminescent analysis for a clinical test is disclosed, for example, in European Patent Publication No. 82636 and U.S. Pat. No. 4,745,181.

Known acridinium esters include those having hydrophilic structures such as those containing sulfonium ions at ends [Japanese Patent Application Laid-Open (Kokai) No. HEI 5-255264], those containing hydrazonium ions in spacer portions [Japanese Patent Application Laid-Open (Kokai) No. HEI 5-255263], and those obtained by substituting a carboxyl group for the methyl group or the like of acridinium [Japanese Patent Application Laid-Open (Kokai) No. HEI 6-228102]. These acridinium esters having hydrophilic structures are practically intended to label amino groups, and are considered to be compounds suitable for labeling amino acids, proteins and the like and hence for use in immunoluminescent analyses for clinical tests.

Incidentally, analytes in immunoluminescent analyses for clinical tests are mostly amino acids and proteins. As these substances contains many amino groups, the above-described known acridinium compounds have a significant advantage in that labeling can be easily performed.

In contrast, they label amino groups contained abundantly in amino acids and proteins. As a result, there are many site to be labeled. This has led to problems in the uniformity and reproducibility of labeling, the problem of insolubilization of analytes such as antibody proteins, and a problem that, when labeling is effected to an antibody, a labeling compound binds to amino groups located at antigen recognition sites and its function as an antibody is reduced or lost. When an analyte is a low-molecular substance, that is, contains only a limited number of amino groups, it may be possible to control a labeling reaction and to readily perform labeling at a constant molar ratio. However, when an analyte is a high-molecular substance such as an antibody protein and the number of amino groups cannot be precisely determined, there is a drawback that conditions for permitting labeling at a constant molar ratio have to be provisionally ascertained through repeated trial and error.

Incidentally, to furnish a compound as a chemiluminescent labeling reagent for practical use, it is essential that the compound assures an easy labeling reaction and does not result in luminescence or decomposition under labeling conditions. Counterparts to be labeled by an acridinium ester vary widely, led by low-molecular compounds such as amino acids and including even high-molecular compounds such as enzymes and antibodies. When amino groups of an analyte are relied upon as described above, an imide group is often introduced into an acridinium ester to make it bind to amino groups as disclosed in the publications referred to above. When a binding reaction to amino groups is performed using this imide group, the reaction proceeds efficiently under alkaline conditions. However, an acridinium compound is an unstable compound so that it results in luminescence or decomposition under alkaline conditions. Efficient performance of labeling while retaining luminescent activity therefore requires mutually contradictory reaction conditions and is not conveniently feasible.

It has accordingly been desired to find out a labeling compound capable of binding to an analyte such as an amino acid or protein under mild conditions in a chemiluminescent labeling method useful in an immunoluminescent analysis or the like and having sufficient binding force while possessing high specificity, and further to provide a method for stably and accurately detecting the analyte by making use of the labeling compound.

DISCLOSURE OF THE INVENTION

To solve the above-described problems, the present inventors first hinted upon using, as groups to be labeled, SH groups instead of amino groups used to date because SH groups have good reactivity although they are generally not abundantly contained in amino acids, proteins or the like. The present inventors have then found that an acridinium compound with a maleimide group introduced therein can be advantageously used as an SH-labeling reagent for labeling such SH groups, leading to the completion of the present invention.

An object of the present invention is therefore to provide an SH-labeling reagent comprising an acridine compound represented by the following formula (I):

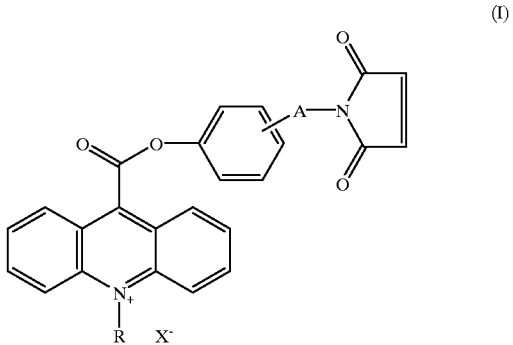

wherein

A represents the following group:

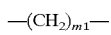

or

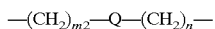

in which Q represents a group —S$^+$RX$^-$—, a group —N$^+$RR$_1$X$^-$— wherein R$_1$ represents an alkyl group having 1 to 6 carbon atoms or an aryl group, a group

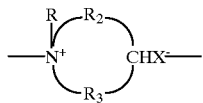

wherein $R_2$ and $R_3$ may be the same or different and are each independently a group $-(CH_2)_k-$ (k: a number of 1 to 3) or $-O(CH_2CH_2O)_l-$ (l: a number of 1 to 3),
m1 stands for a number of 1 to 6,
m2 denotes a number of 0 to 2,
n means a number of 1 to 2;
R represents an alkyl group having 1 to 6 carbon atoms or an aryl group; and
$X^-$ represents an anion.

Another object of the present invention is to provide an SH-labeling reagent comprising an intermediate for the above-described acridine compound, that is, an acridine compound represented by the following formula (II):

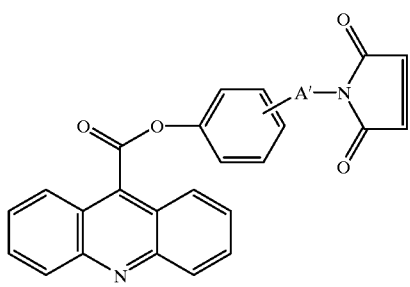

(II)

wherein
A' represents the following group:

$-(CH_2)_{m1}-$ or $-(CH_2)_{m2}-Q'-(CH_2)_n-$ in which Q' represents a group $-S-$, a group $-NR_1-$ wherein $R_1$ represents an alkyl group having 1 to 6 carbon atoms, a group

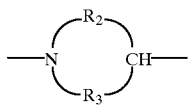

wherein $R_2$ and $R_3$ may be the same or different and are each independently a group $-(CH_2)_k-$ (k: a number of 1 to 3) or $-O(CH_2CH_2O)_l-$ (l: a number of 1 to 3), and
m1, m2 and n have the same meanings as defined above.

A further object of the present invention is to provide processes for the preparation of the acridine compounds represented by the formulas (I) and (II), respectively.

A still further object of the present invention is to provide a method for labeling an analyte by using the above formula (I) or (II).

BEST MODE FOR CARRYING OUT THE INVENTION

The compound represented by the formula (I), which pertains to the present invention, can be prepared, for example, in accordance with one of the following Processes 1 or 2.

Process 1

Among acridine compounds according to the present invention, each compound (Ia) in which A is a group $-(CH_2)_{m1}-$, wherein m1 has the same meaning as defined above, can be obtained by reacting an alkylating agent (III) with a compound represented by the formula (IIa) [hereinafter called the "intermediate (IIa)"] in a manner known per se in the art in accordance with the following reaction formula.

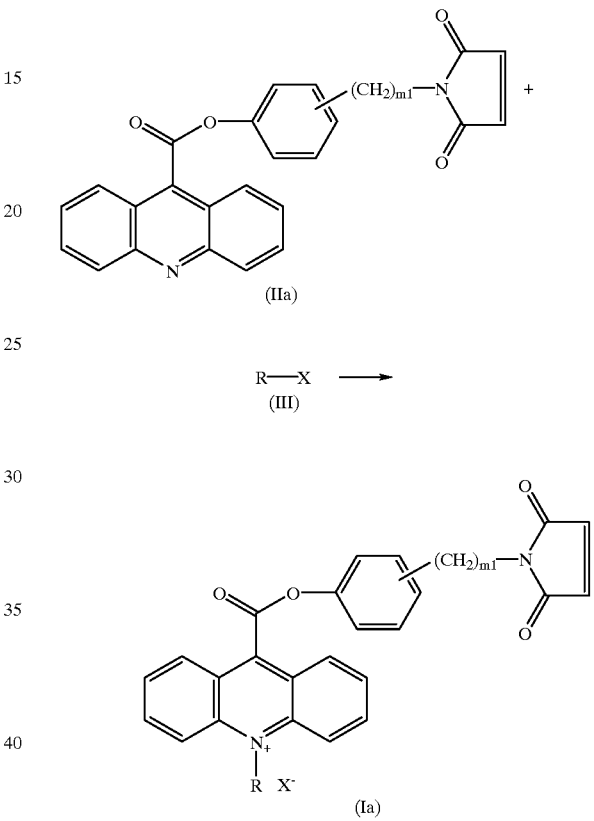

wherein X represents an eliminative group readily convertible into an anion, and R and m1 have the same meanings as defined above.

Illustrative of the alkylating agent (R—X) employed in the above reaction are alkyl halides such as methyl iodide, ethyl bromide and ethyl iodide, methyl trifluoromethanesulfonate, methyl fluorosulfonate, methyl methanesulfonate, and methyl p-toluene sulfonate. Accordingly, $X^-$ in the formula (Ia) may most typically be a halogen ion such as $I^-$ or $Br^-$, $CF_3SO_3^-$, $FSO_3^-$, $CH_3SO_3^-$, or $p-CH_3C_6H_4SO_3^-$, and R is an alkyl group having 1 to 6 carbon atoms such as methyl or ethyl or an aryl group. As a solvent useful in the above reaction, ethyl ether, toluene, acetonitrile or the like can be exemplified.

The intermediate (IIa), which is a starting material for the preparation of the compound (Ia), can be prepared by reacting an ω-aminoalkylenephenyl 9-acridinecarboxylate (IV) and maleic anhydride (V) in the presence of a base in accordance with the following reaction formula.

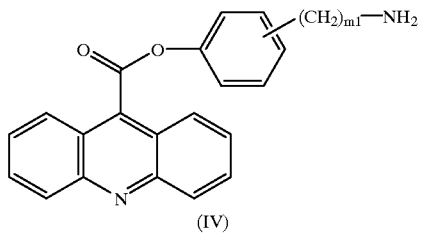
(IV)

+

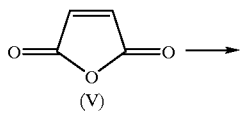
(V) →

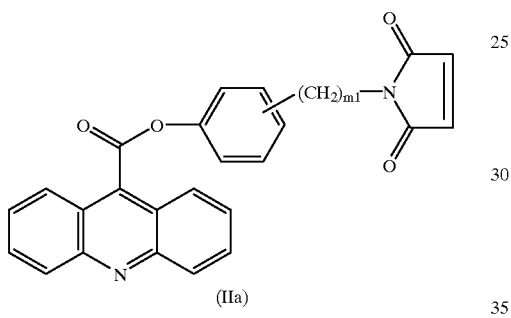
(IIa)

wherein m1 has the same meaning as defined above.

Specifically, the compound (II) can be obtained, for example, by reacting the compounds (IV) and (V) at a temperature of 80 to 140° C. or so while using sodium acetate, potassium carbonate or the like as a base and acetic acid, propionic acid or the like as a solvent in accordance with the process disclosed in Clin. Chem. 31(10), 1664–1668, 1985.

Incidentally, the above intermediate (IIa) is disclosed in the form of a general formula in Japanese Patent Application Laid-Open (Kokai) No. SHO 62-61969. However, this patent publication does not contain any disclosure, to say nothing of a working example, which may provide a clue for the preparation of this compound. As a matter of fact, this compound is therefore believed to be a novel compound.

Process 2

Among the acridine compounds according to the present invention, each compound (Ib) in which A is a group —$(CH_2)_{m2}$—Q'—$(CH_2)_n$—, wherein Q', m2 and n have the same meanings as defined above, is a novel compound and as specific examples of this compound, compounds of the following formulas can be mentioned.

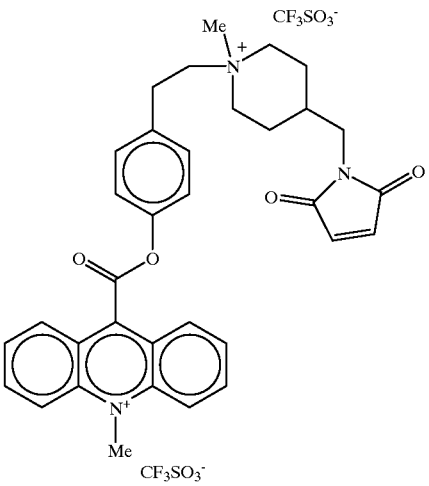
(6)

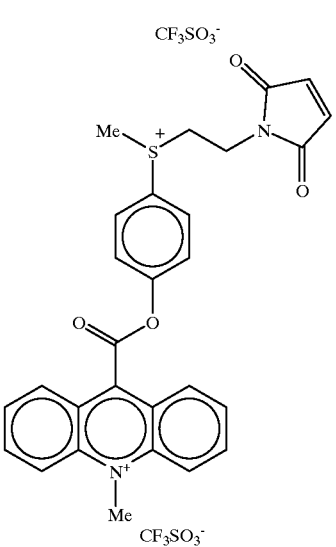
(12)

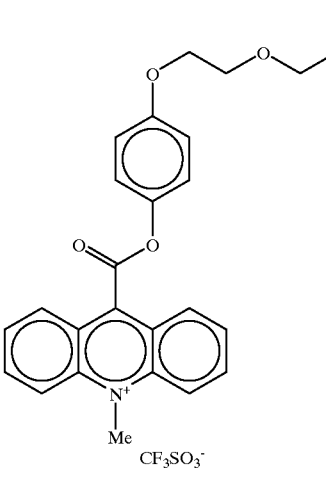
(20)

The compound (Ib) can be obtained, for example, by reacting an alkylating agent (III) with a compound represented by the formula (IIb) [hereinafter called the "intermediate (IIb)"] in a manner known per se in the art in accordance with the following reaction formula.

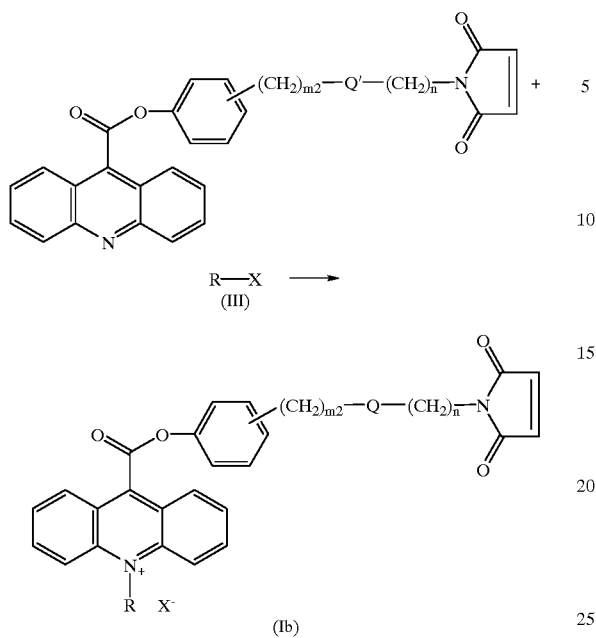

wherein Q, Q', R, X⁻, m2 and n have the same meanings as defined above.

As the alkylating agent (R—X) for use in the this reaction, one employed in Process 1 can be mentioned. Accordingly, $X^-$ in the formula (Ib) may most typically be a halogen ion such as $I^-$ or $Br^-$, $CF_3SO_3^-$, $FSO_3^-$, $CH_3SO_3^-$, or $p\text{-}CH_3C_6H_4SO_3^-$, and R is an alkyl group having 1 to 6 carbon atoms such as methyl or ethyl or an aryl group. As a solvent useful in the above reaction, ethyl ether, toluene, acetonitrile or the like can be exemplified.

Further, the intermediate (IIb) as a raw material for the preparation of the compound (Ib) is a novel compound. As specific examples of this compound, compounds represented by the following formulas can be exemplified.

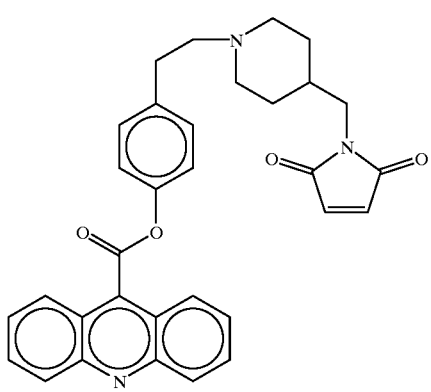

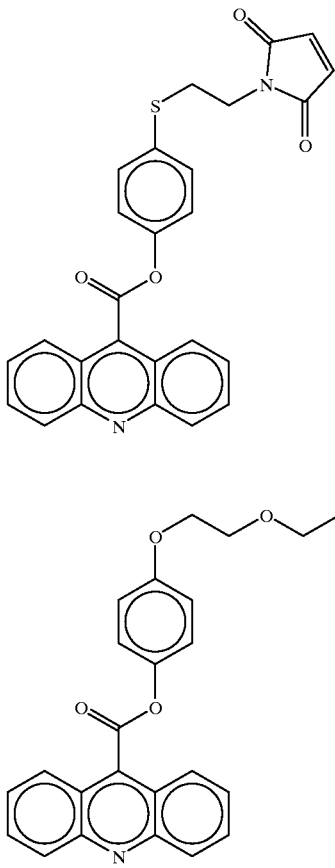

The intermediate (IIb) can be prepared by any one of the following processes.

(i) In accordance with the following reaction scheme, an eliminative-group-containing phenol compound (VI) and a reactive derivative (VII) of 9-acridinecarboxylic acid are reacted to prepare an acridine ester derivative (VIII) having the eliminative group at an end; a polyamine (IX) having a primary amino group at an end thereof, which may have been protected by a protecting group as needed, and a primary or secondary amino group at an opposite end thereof is reacted to the acridine ester derivative in the presence of a suitable base to prepare an acridine ester (X) having at an end thereof the primary amino group which may have been protected by the protecting group as needed; when there is the protecting group for the terminal primary amino group, the protecting group is eliminated, and maleic anhydride (V) and the primary amino group are then reacted into a maleimide group, whereby a compound (IIb') is obtained.

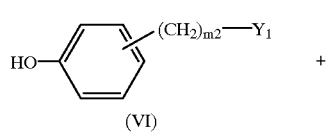

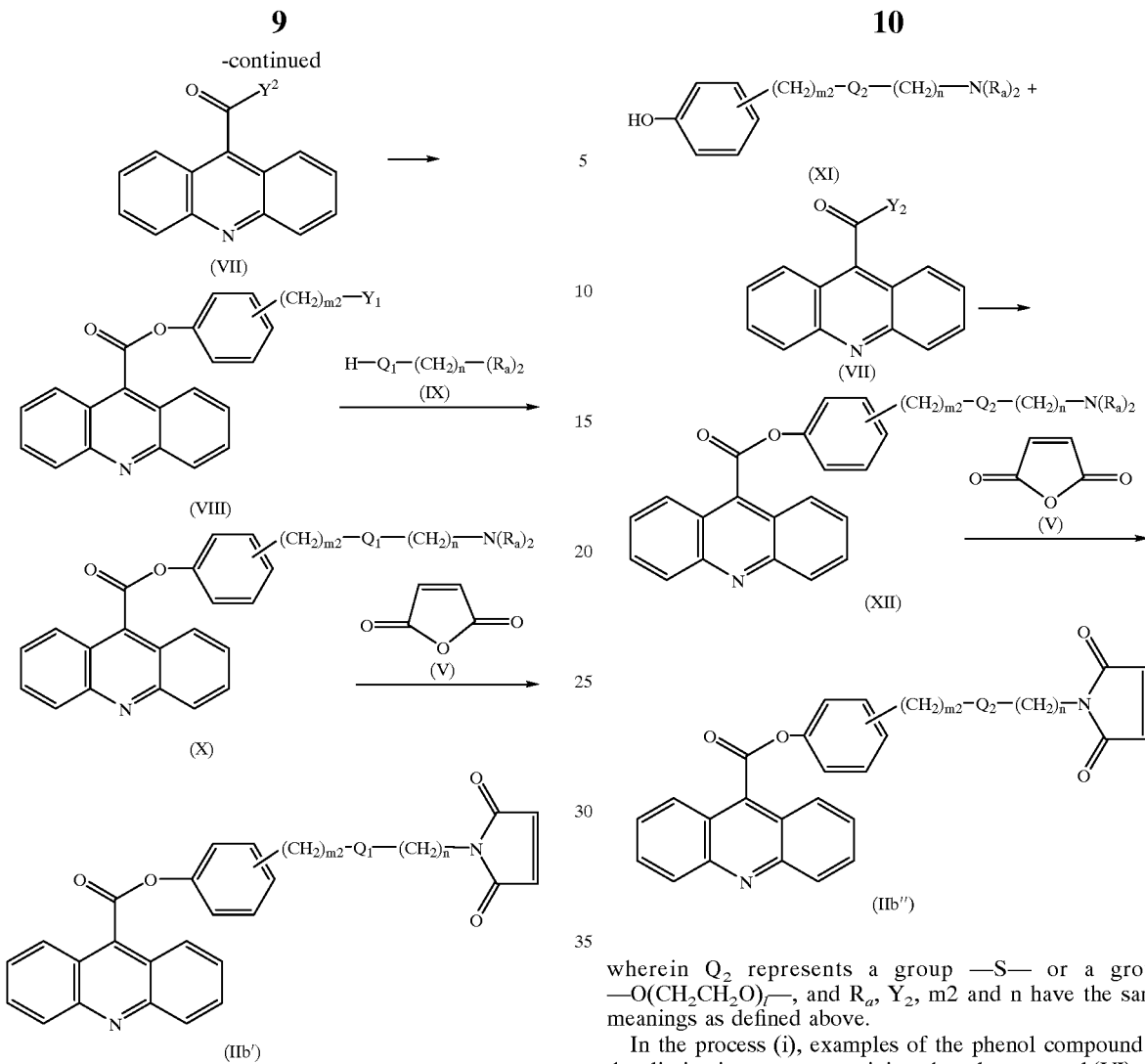

wherein $R_a$s are each independently a hydrogen atom or an amino-protecting group, $Y_1$ and $Y_2$ represent eliminative groups, and $Q_1$ represents a group —$NR_1$— or a group

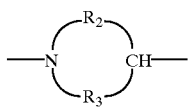

wherein $R_2$ and $R_3$ have the same meanings as defined above, and m2 and n have the same meanings as defined above.

(ii) In accordance with the following reaction scheme, a phenol derivative (XI) having a thioether or polyether with a primary amino group protected with a protecting group and bonded to an end thereof and a reactive derivative (VII) of 9-acridinecarboxylic acid are reacted to prepare an acridinium ester (XII), and subsequent to deprotection of the terminal amino group, maleic anhydride (V) is reacted to the terminal primary amino group to convert it into a maleimide group, whereby a compound (IIb″) is obtained.

wherein $Q_2$ represents a group —S— or a group —O(CH$_2$CH$_2$O)$_f$—, and $R_a$, $Y_2$, m2 and n have the same meanings as defined above.

In the process (i), examples of the phenol compound in the eliminative-group-containing phenol compound (VI) can include 4-(tosyloxymethyl)phenol, 4-(3-chloropropyl) phenol and 4-(2-tosyloxyethyl)phenol, and examples of its eliminative group can include tosyloxy, mesyloxy and halogen atoms (Cl, Br, I). On the other hand, illustrative of the reactive derivative (VII) of 9-acridinecarboxylic acid are acid halides such as chloride and bromide, acid anhydrides and active acid esters. Further, examples of the polyamine (IX) can include N-(2-aminoethyl)piperazine, 1,3-diaminopropane and 4-(aminomethyl)piperidine, and examples of its protecting group can include t-butoxycarbonyl (Boc), benzyloxycarbonyl (Cbz) and phthalimide. In addition, illustrative of the bases employed in the reaction of the compounds (VI) and (VII) and the reaction of the compounds (VIII) and (IX) are triethylamine and pyridine. Illustrative solvents usable in the above reactions can include methylene chloride, chloroform (CHCl$_3$), ethyl ether, toluene, and pyridine.

To conduct elimination of the protecting group of the primary amino group from the compound (IX), the deprotection can be carried out in a solventless manner or in a suitable solvent by using an acid, catalytic reduction conditions or a base in a manner known per se in the art. Usable examples of the acid can include boron trifluoride (BF$_3$), trifluoroacetic acid and hydrochloric acid. Examples of a catalyst for the catalytic reduction can include palladium-carbon, palladium black and platinum black. Illustrative of the base are hydrazine, sodium hydroxide and potassium hydroxide. Exemplary solvents can include ethyl ether, 1,4-dioxane, methanol, ethanol, water, acetonitrile and acetic acid.

Further, the maleimidation of the primary amino group in the compound (X), from which the protecting group has been eliminated as needed, can be conducted by heating the compound in the presence of maleic anhydride and a base under heat in a solvent and reacting the maleic anhydride with the primary amino group. Usable examples of the base can include sodium acetate and potassium carbonate. Examples of the solvent can include acetic acid and propionic acid.

On the other hand, among the phenol derivatives (XI) having a thioether or polyether structure and containing a terminal amino group as referred to in connection with the process (ii), examples of the phenol derivative having thioether can include 4-(2-aminoethylthio)phenol and 4-(3-aminopropylthio)phenol, and examples of the phenol derivative having a polyether structure can include 4-[3-(2-aminoethoxy)propyloxy]phenol and 4-[2-(2-aminoethoxy)ethoxy]phenol. As exemplary protecting groups for these amino groups, Boc, Cbz, phthalimide and the like can be mentioned. Further, usable examples of the base can include triethylamine and pyridine, whereas illustrative of the solvent are methylene chloride, ethyl ether, toluene and pyridine.

The deprotection and maleimidation of the primary amino group can be effected by methods similar to those described in connection with the process (i).

A description will next be made of a method for reacting the compound (I) according to the present invention to SH groups in an amino acid or a protein to label the substance.

For example, to label an antibody with the compound (I) according to the present invention, the antibody is first digested with pepsin to obtain F(ab')$_2$, which is then reduced under mild conditions to prepare Fab'. The maleimide group in the invention compound (I) is next reacted to SH groups of the Fab' in a solution, whereby labeling can be achieved.

The reaction between Fab' and the invention compound (I) can be conducted by reacting Fab' and the invention compound (I) at a molar ratio of 1:1 to 1:10, in an aqueous solution of pH 5 to 7, preferably pH 6 to 6.5 at a temperature of 1 to 37° C., preferably 4 to 10° C. for 10 minutes to 72 hours, preferably about 48 hours while protecting SH groups from oxidation by oxygen dissolved in the reaction solution by using approximately 1 to 5 mM EDTA.

Labeling by the compound (I) can generally be conducted in an aqueous medium at pH 7 or lower. If an analyte is sparingly soluble or insoluble in water, labeling can be conducted in a manner to be described hereinafter. Namely, water is added to a solution of the analyte in a small amount of an inert solvent which is well miscible with water (hereinafter called the "inert solvent"), whereby an aqueous solution of the analyte is prepared. In the solution, an aqueous solution of the compound (I) is mixed to conduct a reaction between SH groups and maleimide groups at pH 7 or lower. This reaction proceeds as a result of nucleophilic addition of the analyte to the unsaturated bonds of the maleimide group in the compound (I) of the present invention. Even when amino groups are contained in addition to SH groups in the analyte, the nucleophilicity of the amino groups is however suppressed and no reaction product with amino groups is formed, because the reaction is conducted at pH 7 or lower. It is here that the compound of the present invention can be used as a selective reagent for SH groups.

Illustrative of the inert solvent employed in the labeling are N,N-dimethylacetamide, dimethylsulfoxide, N,N-dimethylformamide (DMF), 1,4-dioxane and pyridine.

After the labeling, the labeled analyte can be isolated by a separation method such as gel chromatography, ion-exchange chromatography, affinity chromatography or high-performance liquid chromatography. Namely, labeling at a constant molar ratio is feasible by the above-described method.

Even when an analyte does not contain SH groups, the labeling method of this invention can be applied by introducing SH groups to hydroxyl groups, amino groups and/or the like in the analyte under mild conditions by using S-acetylmercaptosuccinic anhydride or the like. In this case, a quantitation of introduced SH groups makes it possible to estimate the molar ratio of the analyte and SH groups. Accordingly, analytes to which the labeling method of this invention can be applied can be any substances insofar as these substances contain SH groups or permit introduction of SH groups. Even low molecular substances such as amino acids can be labeled with the compound (I) of the present invention under mild conditions in a similar manner as that described above.

The labeled substance obtained as described above can be caused to produce chemiluminescence under known luminescent conditions for acridinium esters, for example, by the addition of $H_2O_2$ or the like under alkaline conditions. By detecting this luminescence with a chemiluminescence detector, the existence of the substance can be ascertained. Further, from the quantity of the chemiluminescence, the quantity of the labeled substance can be determined. The labeling method can therefore be applied to the tracing of in vivo distributions of medicines and to qualitative analyses and quantitative analyses in various fields such as diagnostics, all of which require detection of trace quantities.

A description will next be made about specific application examples of the labeling method making use of the compound (I) according to the present invention.

As an application of the labeling method of this invention, there is, for example, a measuring method of an analyte in a sample, which comprises capturing the analyte by a binding reaction between the analyte and a substance which has been conjugated on a carrier and specifically binds to the analyte, as in the so-called chemiluminescent immunoassay sandwich method; causing a substance, which also specifically binds to the analyte and has been labeled with the compound (I) of this invention, to bind to the thus-captured analyte; and then measuring the intensity of luminescence.

There is also a measuring method of an analyte in a sample, which as in the so-called chemiluminescent competitive immunoassay, comprises labeling the analyte with the compound (I) of the present invention; adding beforehand the labeled analyte at a predetermined concentration; then measuring the intensity of luminescence from the labeled analyte while using a reaction that, to a substance which specifically binds to both the analyte in the sample and the labeled analyte, these analytes competitively bind.

In these cases, examples of combinations of specifically binding substances can include an antigen and an antibody, a nucleic acid and its complementary sequence, an effector molecule and a receptor molecule, an enzyme and an inhibitor, avidin and biotin, and a substance containing a saccharide chain and its corresponding lectin.

As another application, there is, for example, a measuring method of an analyte, which as in the so-called post-column high-performance liquid chromatography, labeling the analyte with the compound (I) of the present invention; isolating the labeled analyte by the above-described separation method such as chromatography; then measuring the analyte by a chemiluminescence detector.

In the above-described labeling methods, the compound (I) of the present invention can overcome the drawbacks of the conventionally-known acridinium esters, that is, various problems such as the insolubilization of a labeled analyte, the potential inactivation of amino groups, even those required for bioactivity, the difficulty in binding at a constant binding molar ratio, the difficulty in establishing reproducibility in binding reactions, and premature luminescence and decomposition even under binding reaction conditions.

As a further application example of the present invention, the following method can be mentioned. Namely, the intermediate (II) which is also used for the synthesis of the compound (I) according to the present invention is reacted in advance with an SH-containing analyte (hereinafter called "prelabeling"). An appropriate N-alkylating agent is then reacted, and under alkaline conditions, an adequate chemiluminescent agent such as $H_2O_2$ is caused to act. Resulting chemiluminescence is detected by a chemiluminescence detector to measure the analyte.

In the acridine ester represented by the formula (II), the terminal maleimide group has binding activity to SH groups. Moreover, it can be isolated as a stable compound. It can therefore be caused to bind to an SH-containing substance in advance.

The above-described binding method in the pre-labeling reaction of the analyte by the intermediate (II), the isolation method of the pre-labeled analyte and the like can be conducted in substantially the same manners as in the method making use of the compound (I).

The above-described pre-labeled analyte can be converted further into an acridinium-ester-labeled analyte by reacting it with the alkylating agent (III) in a suitable solvent. Usable examples of the alkylating agent (III) can include alkyl halides such as methyl iodide, ethyl iodide and ethyl bromide, methyl trifluoromethanesulfonate, methyl fluorosulfonate, methyl methanesulfonate and methyl p-toluenesulfonate as described above. Further, illustrative of usable solvents are tetrahydrofuran and acetonitrile in addition to the solvents employed above-described labeling reactions.

When the acridinium-ester-labeled analyte deposits as crystals from the used solvent subsequent to the reaction, it can be isolated by filtration. When it does not deposit, it can be isolated by column chromatography.

Subsequent to the pre-labeling reaction by the intermediate (II), the reaction product is further N-alkylated with the alkylating agent (III). Chemiluminescence from the thus-labeled analyte and its use or the like are similar to those described in connection with the compound (I).

Incidentally, the labeling method making use of the intermediate (II) is not suited for an analyte which also contains other groups active to the alkylating agent in addition to SH groups, in view of the labeling with the alkylating agent (III) subsequent to the binding. In such a case, it is necessary to take a measure such as protecting these active groups with protecting groups.

The present invention will hereinafter be described more specifically by the following examples. It should however be borne in mind that the present invention is not limited to or by these examples.

EXAMPLE 1

Synthesis of 4-(2-tosyloxyethyl)phenol (1)

4-Hydroxyphenethyl alcohol (3.2 g) was dissolved in 50 ml of pyridine, to which 4.0 g of tosyl chloride was added in small portions under ice cooling. The temperature of the reaction mixture was allowed to rise to room temperature, at which it was stirred for 2 hours. Then, insoluble matter was filtered off, and pyridine was distilled off under reduced pressure. The residue was isolated and purified by chromatography on a silica gel column (eluent: $CHCl_3$), whereby 3.4 g of the compound (1) were obtained (yield: 59%).

EXAMPLE 2

Synthesis of 9-acridinecarboxylic acid chloride (2)

Thionyl chloride (20 me) was added to 2.2 g of 9-acridinecarboxylic acid, followed by heating under reflux for 5 hours. After the thionyl chloride was distilled off under reduced pressure, 20 ml of methylene chloride were added further. Distillation was repeated twice under reduced pressure, whereby 2.4 g of the compound (2) were obtained (yield: stoichiometric).

EXAMPLE 3

Synthesis of 4-(2-tosyloxyethyl)phenyl 9-acridine carboxylate (3)

In 30 ml of pyridine, 2.4 g of the compound (2) obtained in Example 2 were dissolved. Under ice cooling and stirring, 2.9 g of the compound (1) obtained in Example 1 were added in small portions. Subsequent to stirring at room temperature for 2 hours, the pyridine was distilled off under reduced pressure. $CHCl_3$ was added further, and distillation was repeated twice under reduced pressure. The residue was isolated and purified by chromatography on a silica gel column (eluent: $CHCl_3$), whereby 2.7 g of the compound (3) were obtained (yield: 54%).

EXAMPLE 4

Synthesis of 4-[2-(4-aminomethylpiperidin-1-yl) ethyl]phenyl 9-acridinecarboxylate (4)

In 30 ml of DMF, 2.9 g of the compound (3) obtained in Example 3 were dissolved, followed by the addition of 0.59 g of 4-aminomethylpyridine. The resultant mixture was stirred at room temperature, to which 0.60 g of t-BuOK was added under ice cooling. The thus-obtained mixture was stirred at room temperature for 5 hours. The DMF was distilled off under reduced pressure, and the residue was dissolved in $CHCl_3$. The solution so obtained was washed with water and then dried over anhydrous magnesium sulfate ($MgSO_4$). The solvent was distilled off under reduced pressure. The residue was isolated and purified by chromatography on a silica gel column (eluent: $CHCl_3/MeOH=7/3$), whereby 0.41 g of the compound (4) was obtained (yield: 18%).

EXAMPLE 5

Synthesis of 4-[2-[4-[(maleimid-1-yl)methyl] piperidin-1-yl]ethyl]phenyl 9-acridinecarboxylate (5)

Into 20 ml of acetic acid, 0.41 g of the compound (4) obtained in Example 4, 0.30 g of maleic anhydride and 0.30 g of sodium acetate were added, followed by heating under reflux for 3 hours. The acetic acid was then distilled off under reduced pressure. Water was added to the residue, followed by extraction with $CHCl_3$. The extract was dried over $MgSO_4$, and the $CHCl_3$ was distilled off under reduced pressure. The residue was purified by chromatography on a silica gel column (eluent: $CHCl_3$), whereby 0.22 g of the compound (5) was obtained (yield: 43%). Analysis data of this substance are shown below.

NMR (CDCl$_3$) δ: 8.3(m,4H), 8.0–7.6(m,4H), 7.3(s-like, 4H), 6.7(s,2H), 3.4(d,J=7,2H), 3.1–2.5(m,6H), 2.2–1.5(m, 7H).

MASS (FAB): 520 (M+1).

EXAMPLE 6

Synthesis of 4-[2-[4-(maleimid-1-yl)methyl-1-methylpiperidinium-1-yl]ethyl]phenyl 10-methylacridinium-9-carboxylate (6)

In 20 ml of toluene, 0.22 g of the compound (5) obtained in Example 5 was dissolved, to which 0.30 g of methyl trifluoromethanesulfonate was added at room temperature under stirring. After the resulting mixture was stirred at room temperature for 1 hour, it was allowed to stand overnight. A red deposit was collected by filtration, washed with toluene and then dried in air, whereby 30 mg of the compound (6) were obtained (yield: 9.2%). Analysis data of this substance are shown below.

NMR (DMSO-d$_6$) δ: 8.8–8.0(m,8H), 7.5(s-like,4H), 6.8 (s,2H), 5.1(s,3H), 3.3(s,3H), 3.7–3.0(m,10H), 2.0–1.6(m, 5H).

MASS (FAB): 550 (M+1).

EXAMPLE 7

Synthesis of 4-(2-aminoethylthio)phenol (7)

To 30 ml of ethanol, 1.2 g of 4-mercaptophenol, 2.1 g of 2-bromoethylamine hydrochloride and 1.4 g of potassium carbonate were added, followed by stirring for 3 hours at room temperature. Water was added, and the resulting mixture was extracted with ethyl ether. The extract was dried over MgSO$_4$ and the ethyl ether was distilled off under reduced pressure, whereby 1.7 g of the compound (7) were obtained (yield: stoichiometric).

EXAMPLE 8

Synthesis of 4-(2-N-Boc-aminoethylthio)phenol (8)

In 30 ml of acetonitrile, 1.7 g of the compound (7) obtained in Example 7 were dissolved. Anhydrous Boc (2.4 g) was added, followed by stirring for 1 hour. After the solvent was distilled off under reduced pressure, pyridine was added. The pyridine was then distilled off under reduced pressure, whereby 2.7 g of the compound (8) were obtained (yield: stoichiometric).

EXAMPLE 9

Synthesis of 4-(2-N-Boc-aminoethylthio)phenyl 9-acridinecarboxylate (9)

In 30 ml of pyridine, 2.4 g of the compound (2) obtained in Example 2 were dissolved, to which 2.7 g of the compound (8) obtained in Example 8 were added in small portions under ice cooling and stirring. After the resulting mixture was stirred at room temperature for 2 hours, pyridine was distilled off under reduced pressure. CHCl$_3$ was added further, and distillation was conducted twice under reduced pressure. The residue was isolated and purified by chromatography on a silica gel column (eluent: CHCl$_3$), whereby 3.2 g of the compound (9) were obtained (yield: 68%).

EXAMPLE 10

Synthesis of 4-(2-aminoethylthio)phenyl 9-acridinecarboxylate (10)

To 1.9 g of the compound (9) obtained in Example 9, 20 ml of CF$_3$CO$_2$H were added, followed by stirring at room temperature for 30 minutes. The CF$_3$CO$_2$H was distilled off under reduced pressure, whereby 1.4 g of the compound (10) were obtained (yield: stoichiometric).

EXAMPLE 11

Synthesis of 4-[2-(maleimid-1-yl)ethylthio]phenyl 9-acridinecarboxylate (11)

Into 20 ml of acetic acid, 1.4 g of the compound (10) obtained in Example 10, 1.0 g of maleic anhydride and 1.0 g of sodium acetate were added, followed by heating under reflux for 3 hours. The acetic acid was then distilled off under reduced pressure. Water was added to the residue. The resulting mixture was extracted with CHCl$_3$. The extract was dried over MgSO$_4$, and the CHCl$_3$ was distilled off under reduced pressure. The residue was purified by chromatography on a silica gel column (eluent: CHCl$_3$), whereby 1.1 g of the compound (11) were obtained (yield: 63%). Analysis data of this substance are shown below.

NMR (CDCl$_3$) δ: 8.3(m,4H), 8.0–7.6(m,4H), 7.3(s-like, 4H), 6.7(s,2H), 3.8(t,J=7,2H), 3.2(t,J=7,2H).

MASS (FAB): 455 (M+1).

EXAMPLE 12

Synthesis of 4-[[2-(maleimid-1-yl)ethyl]methylsulfonium]phenyl 10-methylacridinium-9-carboxylate (12)

In 20 ml of toluene, 0.90 g of the compound (11) obtained in Example 11 was dissolved. Under stirring at room temperature, 1.0 g of methyl trifluoromethanesulfonate was added, followed by stirring at room temperature for 1 hour. The reaction mixture was then allowed to stand overnight. A red deposit was collected by filtration, washed with toluene and then dried in air, whereby 1.1 g of the compound (12) were obtained (yield: 71%). Analysis data of this substance are shown below.

NMR (DMSO-d$_6$) δ: 9.0–8.0(m,8H), 7.6(d,J=7,2H), 7.4 (d,J=7,2H), 6.7(s,2H), 5.1(s,3H), 3.8(t,J=7,2H), 3.7(s,3H), 3.2(t,J=7,2H).

MASS (FAB): 467 (M+1).

EXAMPLE 13

Synthesis of 2-(2-N-Boc-aminoethoxy) ethanol (13)

In 30 ml of acetonitrile, 2.1 g of 2-aminoethoxy ethanol were dissolved. Anhydrous Boc (4.8 g) was added, followed by stirring for 1 hour. After the solvent was distilled off under reduced pressure, pyridine was added. The pyridine was then distilled off under reduced pressure, whereby 3.7 g of the compound (13) were obtained (yield: stoichiometric).

EXAMPLE 14

Synthesis of 2-(2-tosyloxyethoxy)-N-Boc-ethylamine (14)

In 50 ml of pyridine, 3.7 g of the compound (13) obtained in Example 13 were dissolved, to which 4.0 g of tosyl chloride were added in portions under ice cooling and stirring. The temperature of the resultant mixture was allowed to rise to room temperature, at which the mixture was stirred for 2 hours. Insoluble matter was filtered off, and the pyridine was distilled off under reduced pressure. The residue was isolated and purified by chromatography on a silica gel column (eluent: CHCl$_3$), whereby 5.5 g of the compound (14) were obtained (yield: 76%).

EXAMPLE 15

Synthesis of 4-[2-(2-N-Boc-aminoethoxy)ethoxy] phenyl benzyl ether (15)

In 30 ml of DMF, 2.0 g of p-benzyloxyphenol were dissolved, to which 1.2 g of t-BuOK were added. After the resulting mixture was stirred at room temperature for 30 minutes, 3.9 g of the compound (14) obtained in Example 14 were added. The mixture so obtained was stirred for 3 hours at room temperature. After the DMF was distilled off under reduced pressure, the residue was dissolved in ethyl ether. The resultant solution was washed once with dilute hydrochloric acid, twice with water, and once with a saturated aqueous solution H of sodium chloride. After the solution was dried over $MgSO_{41}$ the ethyl ether was distilled off under reduced pressure. The residue was purified by chromatography on a silica gel column (eluent: $CHCl_3$), whereby 3.2 g of the compound (15) were obtained (yield: 83%).

EXAMPLE 16

Synthesis of 4-[2-(2-N-Boc-aminoethoxy)ethoxy] phenol (16)

In 40 ml of acetic acid, 3.0 g of the compound (15) obtained in Example 15 were dissolved, to which 2.0 g of palladium black were added. The resulting mixture was then stirred at room temperature for 2 hours under a hydrogen gas atmosphere. The palladium was filtered off, and the filtrate was distilled off under reduced pressure. The residue was isolated and purified by chromatography on a silica gel column (eluent: $CHCl_3/MeOH=9/1$), whereby 2.4 g of the compound (16) were obtained (yield: stoichiometric).

EXAMPLE 17

Synthesis of 4-[2-(2-N-Boc-aminoethoxy)ethoxy] phenyl 9-acridinecarboxylate (17)

In 30 ml of pyridine, 2.4 g of the compound (2) obtained in Example 2 were dissolved. Under ice cooling and stirring, 2.0 g of the compound (16) obtained in Example 16 were added in small portions. After the thus-obtained mixture was stirred at room temperature for 2 hours, the pyridine was distilled off under reduced pressure. $CHCl_3$ was added further, and distillation was performed twice under reduced pressure. The residue was isolated and purified by chromatography on a silica gel column (eluent: $CHCl_3$), whereby 2.1 g of the compound (17) were obtained (yield: 47%).

EXAMPLE 18

Synthesis of 4-[2-(2-aminoethoxy)ethoxy]phenyl 9-acridinecarboxylate (18)

$CF_3CO_2H$ (20 ml) was added to 2.1 g of the compound (17) obtained in Example 17, followed by stirring at room temperature for 30 minutes. The $CF_3CO_2H$ was distilled off under reduced pressure, and water was added. The resulting mixture was neutralized with $NaHCO_3$, and a deposit was then collected by filtration. The filtrate was isolated and purified by chromatography on a silica gel column (eluent: $CHCl_3/MeOH=9/1$), whereby 1.7 g of the compound (18) were obtained (yield: stoichiometric).

EXAMPLE 19

Synthesis of 4-[2-[2-(maleimid-1-yl)ethoxy]ethoxy] phenyl 9-acridinecarboxylate (19)

Into 40 ml of acetic acid, 1.7 g of the compound (18) obtained in Example 18, 1.2 g of maleic anhydride and 1.2 g of sodium acetate were added, followed by heating under reflux for 3 hours. After the reaction mixture was allowed to cool down, the acetic acid was distilled off under reduced pressure. Water was added to the residue, and the resulting mixture was extracted with $CHCl_3$. The extract was dried over $MgSO_4$, and the $CHCl_3$ was distilled off under reduced pressure. The residue was purified by chromatography on a silica gel column (eluent: $CHCl_3$), whereby 0.81 g of the compound (19) was obtained (yield: 42%). Analysis data of this substance are shown below.

NMR ($CDCl_3$) δ: 8.3(m,8H), 7.4–7.0(m,4H), 6.8(s,2H), 4.2(m,2H), 3.9(m,2H), 3.8(s-like,4H).

MASS (FAB): 483 (M+1).

EXAMPLE 20

Synthesis of 4-[2-[2-(maleimid-1-yl)ethoxy]ethoxy] phenyl 10-methylacridinium-9-carboxylate (20)

In 50 ml of toluene, 0.81 g of the compound (19) obtained in Example 19 was dissolved, to which 0.60 g of methyl trifluoromethanesulfonate was added at room temperature under stirring. The resultant mixture was stirred at room temperature for 1 hour and was then allowed to stand overnight. A yellow deposit was collected by filtration, washed with toluene and then dried in air, whereby 0.39 g of the compound (22) was obtained (yield: 37%). Analysis data of this substance are shown below.

NMR (DMSO-$d_6$) δ: 9.0–8.0(m,8H), 7.4(d,J=7,2H), 7.1 (d,J=7,2H), 6.8(s,2H), 5.1(s,3H), 4.2(m,2H), 3.9(m,2H), 3.8 (s-like,4H).

MASS (FAB): 497 (M+1).

EXAMPLE 21

Synthesis of 4-[2-(maleimid-1-yl)ethyl]phenyl 9-acridinecarboxylate (22)

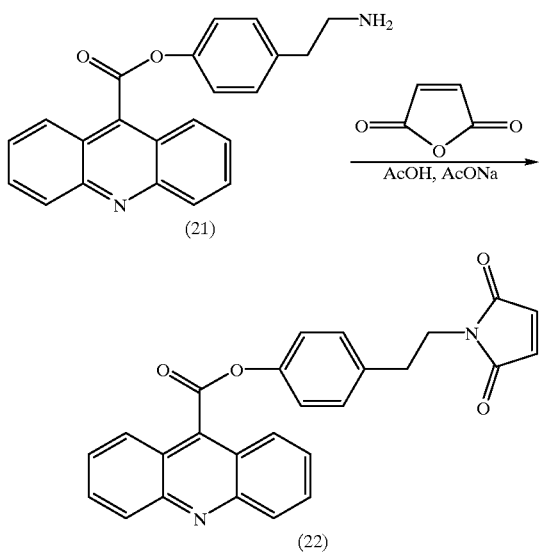

Into 20 ml of acetic acid, 0.71 g of 4-(2-aminoethyl) phenyl 9-acridinecarboxylate (21), 0.60 g of maleic anhydride and 0.60 g of sodium acetate were added, followed by heating under reflux for 3 hours. After the reaction mixture was allowed to cool down, the acetic acid was distilled off under reduced pressure. Water was added to the residue, and the resulting mixture was extracted with $CHCl_3$. The extract was dried over anhydrous magnesium sulfate, and the CHCl₃ was distilled off under reduced pressure. The residue was purified by chromatography on a silica gel column (eluent: CHCl₃), whereby 0.14 g of the compound (22) was obtained (yield: 95%). Analysis data of this substance are shown below.

NMR (CD$_3$OD) δ: 8.2–7.6(m,8H), 7.4(s,4H), 6.8(s,2H), 3.8(t,J=8,2H), 3.0(t,J=8,2H).

MASS (FAB): 423 (M+1).

EXAMPLE 22

Synthesis of 4-[2-(maleimid-1-yl)ethyl]phenyl 10-methylacridinium-9-carboxylate (23)

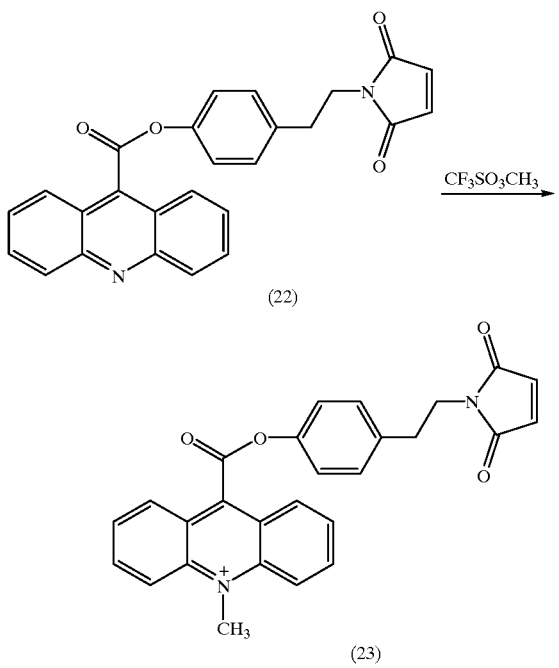

In 20 ml of toluene, 0.17 g of the above-described maleimide (22) was dissolved. To the solution, 0.10 g of methyl trifluoromethanesulfonate was added at room temperature under stirring. After the resultant mixture was stirred at room temperature for 1 hour, it was allowed to stand overnight. After that, a precipitated yellow deposit was collected by filtration and then washed with toluene. The deposit was dried in air, whereby 0.12 g of the compound (23) was obtained (yield: 51%). Analysis data of this substance are shown below.

NMR (CD$_3$OD) δ: 8.9–8.0(m,8H), 7.4(s,4H), 6.8(s,2H), 5.1(s,2H), 3.8(t,J=8,2H), 3.0(t,J=8,2H).

MASS (FAB): 437 (M+1).

EXAMPLE 23

Labeling of antihuman hemoglobin antibody (1) Into 3 ml of a 0.1 M sodium acetate buffer (pH 4.5) containing 0.1 M NaCl, 10 mg of purified antihuman hemoglobin rabbit polyclonal antibody were added. Into this solution, 0.4 g of purified pepsin powder derived from hog gastric juice was added and dissolved. The solution was incubated at 37° C. for 48 hours, whereby the Fc portion of rabbit IgG was digested. By gel filtration making use of a 0.1 M sodium phosphate buffer (pH 6; hereinafter abbreviated as "pH 6 buffer"), which contained 5 mM EDTA, as an eluent and a "Superdex 200 Column" (product of Pharmacia Co., Ltd.), the digestion mixture was fractionated, whereby a solution containing 5 mg of F(ab')₂ in 3 ml of pH 6 buffer was obtained.

2-Mercaptoethylamine (24 mg) were added to the solution, and the resultant mixture was incubated at 37° C. for 24 hours to reduce F(ab')₂ into Fab'. By gel filtration through a "Sephadex G25 Column" (product of Pharmacia Co., Ltd.; eluent: pH 6 buffer), a solution containing 2 mg of Fab' in 3 ml of pH 6 buffer was obtained.

Using a portion of the solution, quantitation of SH groups was conducted by measuring the quantity of 4-mercaptopyridine, which had been obtained as a result of a stoichiometric reaction of 4,4'-dithiopyridine with SH groups of Fab', in terms of absorbance at a wavelength of 324 nm. As a result, Fab' was found to contain one SH group per molecule.

(2) Next, 0.5 ml of pH 6 buffer, which contained 0.04 mg of the compound (6) synthesized in Example 6, was added to 0.75 ml of pH 6 buffer which contained 0.5 mg of Fab'. In other words, they were added so that the molar ratio of Fab' and the compound (6) in their binding reaction became 1:5. The resulting mixture was incubated at 4° C. for 48 hours, whereby Fab' was labeled with the compound (6). After the reaction, gel filtration was conducted through a "Sephadex G25 Column" (product of Pharmacia Co., Ltd.; eluent: pH 6 buffer) to separate the compound (6) added excessively, whereby 0.5 mg of the labeled antibody was obtained in 3 ml of pH 6 buffer (labeled antibody A). The labeled antibody was quantitated from an $E_{280}$ molar absorption coefficient of Fab' and an $E_{260}$ molar absorption coefficient of the compound (6). Fab' and the compound (6) were found to be bound together at a molar ratio of 1 to 1 in the thus-obtained labeled antibody A.

In a similar manner, 0.5 ml of pH 6 buffer, which contained 0.04 mg of the compound (12) synthesized in Example 12, was added to 0.75 ml of pH 6 buffer which contained 0.5 mg of Fab', and after a reaction, gel filtration was conducted, whereby 0.5 mg of a labeled antibody was obtained in 3 ml of pH 6 buffer (labeled antibody B).

Likewise, 0.5 ml of pH 6 buffer, which contained 0.03 mg of the compound (20) synthesized, in Example 20, was added to 0.75 ml of pH 6 buffer which contained 0.5 mg of Fab', and after a reaction, gel filtration was conducted, whereby 0.5 mg of a labeled antibody was obtained in 3 ml of pH 6 buffer (labeled antibody C).

Also as in the above, 0.5 ml of pH 6 buffer, which contained 0.04 mg of the compound (23) synthesized in Example 23, was added to 0.75 ml of pH 6 buffer which contained 0.5 mg of Fab', and after a reaction, gel filtration was conducted, whereby 0.5 mg of a labeled antibody was obtained in 3 ml of pH 6 buffer (labeled antibody D).

In the thus-obtained labeled antibody B, labeled antibody C and labeled antibody D, Fab' and the compound (12), Fab' and the compound (20) and Fab' and the compound (23) were all found to be bound together at a molar ratio of 1 to 1.

EXAMPLE 24

Assay of human hemoglobin by the labeled antibodies

A solution containing 5 μg of purified antihuman hemoglobin mouse monoclonal antibody per 0.1 ml of a 0.05 M phosphate buffer of pH 7 (hereinafter abbreviated as "PBS") containing 0.15 M NaCl therein was prepared. This solution was poured 0.1 ml by 0.1 ml into individual wells of a microplate. The solution was left over at 4° C. for 24 hours, whereby the monoclonal antibody was adsorbed in the form of a solid phase on inner surfaces of the wells.

The solid-phase antibody plate was subjected to blocking treatment with 0.1 ml of PBS which contained 1 mg of bovine serum albumin. On the side, purified human hemoglobin was dissolved in PBS to give 0, 0.2, 1, 5, 25 and 125 μg/ml solutions. 0.1 ml aliquots of these solutions were poured into the individual wells of the microplate, respectively. The solutions were left over at 4° C. for 24 hours, whereby the human hemoglobin in the samples was captured by the solid-phase antibody.

After each well was then washed with PBS to remove unbound human hemoglobin, 0.1 ml of PBS containing 5 μg of the labeled antibody A prepared in Example 23 was poured into each well. The PBS solution was left over at 4° C. for 24 hours to allow a reaction to proceed. Each well was washed with PBS, and subsequent to removal of unbound labeled antibody A, 0.05 ml of 0.1 N NaOH and 0.04 ml of 0.5% $H_2O_2$ were added to produce luminescence. The luminescence was measured by "Luminus CT-9000D" (manufactured by Dia-Iatron Co., Ltd.), which is a microplate reader for measuring chemiluminescence. The quantity of luminescence was measured as an integrated value over 2 seconds.

Likewise, assays of human hemoglobin by the labeled antibody B, labeled antibody C and labeled antibody D were conducted, respectively. The results of the above assays are summarized next in Table 1.

TABLE 1

| Concentration of hemoglobin (μg/ml) | Quantity of chemiluminescence (counts) | | | |
|---|---|---|---|---|
| | Labeled antibody A | Labeled antibody B | Labeled antibody C | Labeled antibody D |
| 0 | 3852 | 3089 | 1655 | 2037 |
| 0.2 | 39410 | 33301 | 18389 | 19527 |
| 1 | 99784 | 88131 | 49136 | 52410 |
| 5 | 255691 | 229749 | 144856 | 149397 |
| 25 | 727500 | 707136 | 501892 | 443599 |
| 125 | 2511377 | 2281501 | 1736876 | 1354858 |

It is evident from Table 1 that the quantities of chemiluminescence produced from the labeled antibody A, the labeled antibody B, the labeled antibody C and the labeled antibody D all increase with the concentration of human hemoglobin and these labeled antibodies are therefore useful for the quantitation of human hemoglobin.

Capability of Exploitation in Industry

The labeling of an analyte by the compound (I) or (II) of the present invention relies upon stable binding between SH groups and maleimide groups and is performed under mild conditions. As a result of labeling under such mild conditions, an antigen recognition site of a labeled antibody or the like, for example, is not impaired and further, an acridine ester is neither consumed through luminescence nor inactivated through decomposition.

Further, the labeling method of this invention relies upon SH groups which are contained in a rather small number in an amino acid or protein. This makes it possible to perform specific labeling to an analyte, leading inter alia to an advantage that binding at a constant binding molar ratio can be achieved between the analyte and a chemiluminescent substance.

When the labeling method of the present invention is applied, for example, to the antibody Fab', the labeling of whole Fab' with the compound (I) [or the intermediate (II)] of the present invention by the addition of the compound even in a somewhat excessive proportion is still labeling at a molar ratio of 1:1 because Fab' contains only one SH group. Moreover, the SH group which takes part in this binding is irrelevant to the bioactive site of Fab' so that the antigen recognition site of Fab' is not impaired.

Accordingly, a qualitative or quantitative analysis of an analyte can be easily achieved from a quantity of chemiluminescence. The labeling method of the present invention can be applied especially to the tracing of in vivo distributions of medicines and the field of diagnostics, all of which require detection of trace quantities.

We claim:

1. An SH-labeling reagent comprising an acridine compound represented by the following formula (I):

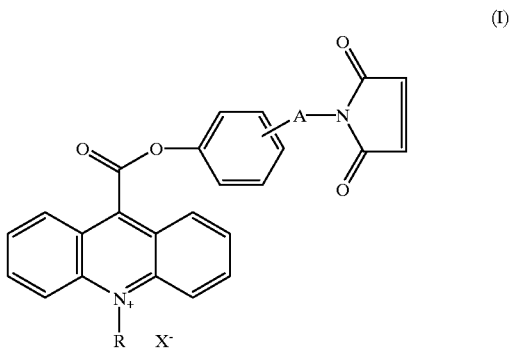

wherein

A represents the following group:

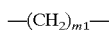

or

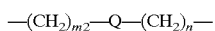

in which Q represents a group —$S^+RX^-$—; a group —$N^+RR_1X^-$— wherein $R_1$ represents an alkyl group having 1 to 6 carbon atoms or an aryl group; a group

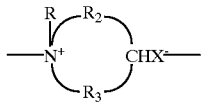

wherein $R_2$ and $R_3$ may be the same or different and are each independently a group —$(CH_2)_k$— (k: a number of 1 to 3); or —$O(CH_2CH_2O)_l$— (l: a number of 1 to 3), m1 stands for a number of 1 to 6, m2 denotes a number of 0 to 2, n means a number of 1 to 2;

R represents an alkyl group having 1 to 6 carbon atoms or an aryl group; and $X^-$ represents an anion.

2. An SH-labeling reagent comprising an acridine compound represented by the following formula (II):

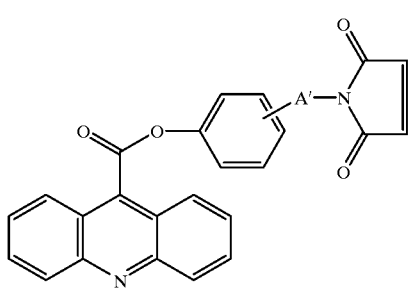

(II)

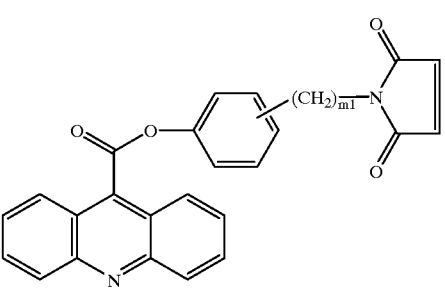

(IIa)

wherein
A' represents the following group:

or

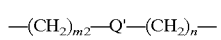

in which Q' represents a group —S—; a group —NR$_1$— wherein R$_1$ represents an alkyl group having 1 to 6 carbon atoms; a group

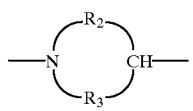

wherein R$_2$ and R$_3$ may be the same or different and are each independently a group —(CH$_2$)$_k$— (k: a number of 1 to 3); or —O(CH$_2$CH$_2$O)$_l$— (l: a number of 1 to 3), and m1, m2 and n have the same meanings as defined above.

3. A process for the preparation of an acridine compound represented by the following formula (Ia):

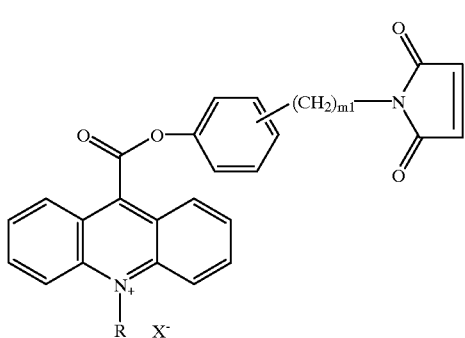

(Ia)

wherein X$^-$ represents an anion, R represents an alkyl group having 1 to 6 carbon atoms or an aryl group, m1 denotes an integer of 1 to 6, which comprises causing an alkylating agent, which is represented by the following formula (III):

 (III)

wherein R has the same meaning as defined above and X represents an eliminative group readily convertible into an anion, to act on an acridine compound represented by the following formula (IIa):

wherein m1 has the same meaning as defined above.

4. A process for the preparation of an acridine compound represented by the following formula (IIa):

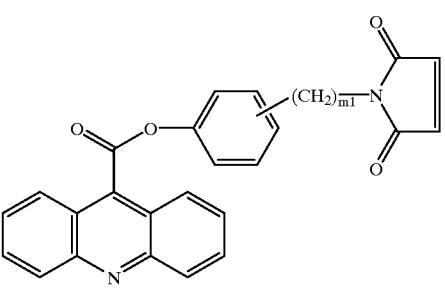

(IIa)

wherein m1 stands for an integer of 1 to 6, which comprises reacting an ω-aminoalkylenephenyl 9-acridinecarboxylate, which is represented by the following formula (IV):

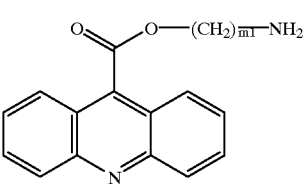

(IV)

wherein m1 has the same meaning as defined above, and maleic anhydride in the presence of a base.

5. An acridine compound represented by the following formula (Ib):

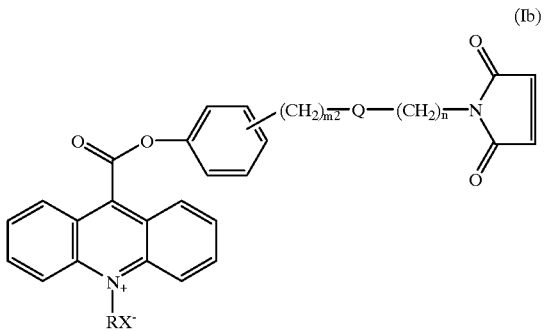

(Ib)

wherein
Q represents a group —S$^+$RX$^-$—; a group —N$^+$RR$_1$X$^-$— wherein R$_1$ represents an alkyl group having 1 to 6 carbon atoms or an aryl group, a group

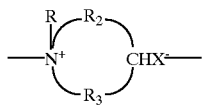

wherein $R_2$ and $R_3$ may be the same or different and are each independently a group $-(CH_2)_k-$ (k: a number of 1 to 3); or a group $-O(CH_2CH_2O)_l-$ (l: a number of 1 to 3);

R represents an alkyl group of 1 to 6 carbon atoms or an aryl group;

$X^-$ represents an anion;

m2 stands for a number of 0 to 2; and n denotes a number of 1 to 2.

6. An acridine compound as an intermediate of the acridine compound represented by the formula (Ib), which is represented by the following formula (IIb):

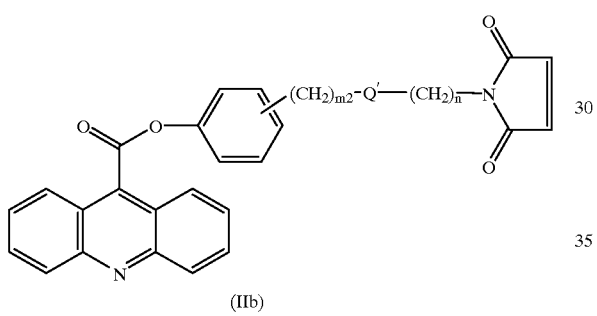

(IIb)

wherein

Q' represents a group —S—; a group $-NR_1-$ wherein $R_1$ represents an alkyl group having 1 to 6 carbon atoms, a group

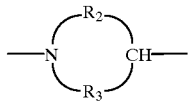

wherein $R_2$ and $R_3$ may be the same or different and are each independently a group $-(CH_2)_k-$ (k: a number of 1 to 3); or $-O(CH_2CH_2O)_l-$ (l: a number of 1 to 3);

m2 stands for a number of 0 to 2; and n denotes a number of 1 to 2.

7. A process for the preparation of an acridine compound represented by the following formula (Ib):

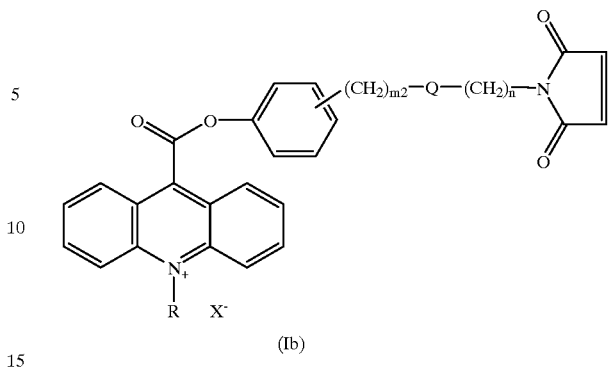

(Ib)

wherein

Q represents $-S^+RX^--$; $-N^+RR_1-$ wherein $R_1$ represents an alkyl group having 1 to 6 carbon atoms or an aryl group, a group

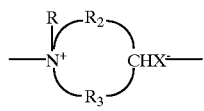

wherein $R_2$ and $R_3$ may be the same or different and are each independently a group $-(CH_2)_k-$ (k: a number of 1 to 3); or a group $-O(CH_2CH_2O)_l-$ (l: a number of 1 to 3);

R represents an alkyl group of 1 to 6 carbon atoms or an aryl group;

X represents an eliminative group readily convertible into an anion;

m2 stands for a number of 0 to 2; and n denotes a number of 1 to 2, which comprises causing an alkylating agent, which is represented by the following formula (III):

$$R—X \quad (III)$$

wherein R and X have the same meanings as defined above, to act on an acridine compound represented by the following formula (IIb):

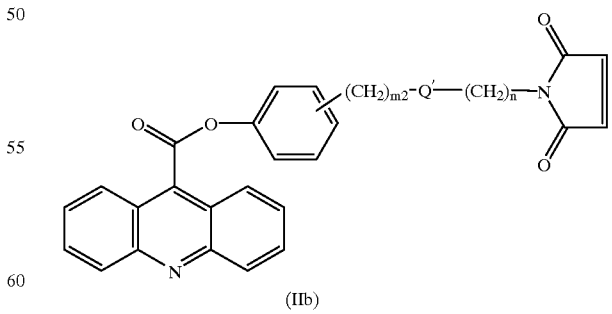

(IIb)

wherein

Q' represents a group —S—; a group $-NR_1-$ wherein $R_1$ represents an alkyl group having 1 to 6 carbon atoms; or a group

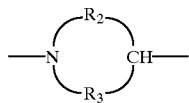

wherein $R_2$ and $R_3$ may be the same or different and are each independently a group $-(CH_2)_k-$ (k: a number of 1 to 3); or $-O(CH_2CH_2O)_l-$ (l: a number of 1 to 3; and m2 and n have the same meanings as defined above.

8. A process for the preparation of an acridine compound represented by the following formula (IIb'):

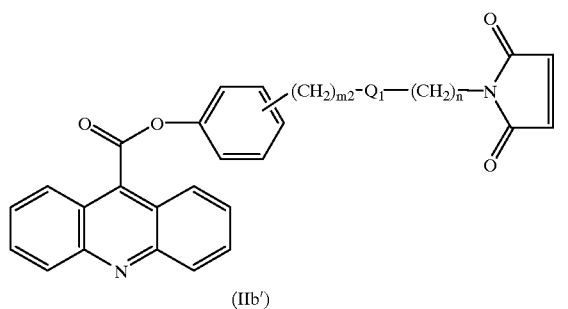

(IIb')

wherein $Q_1$ represents a group $-NR_1-$ wherein $R_1$ represents an alkyl group having 1 to 6 carbon atoms, or

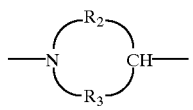

wherein $R_2$ and $R_3$ may be the same or different and are each independently a group $-(CH_2)_k-$ (k: a number of 1 to 3);

m2 stands for a number of 0 to 2; and n denotes a number of 1 to 2, which comprises reacting an eliminative-group-containing phenol compound, which is represented by the following formula (VI):

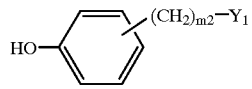

(VI)

wherein $Y_1$ represents an eliminative group and $m_2$ has the same meaning as defined above, with a 9-acridinecarboxylic acid derivative, which is represented by the following formula (VII):

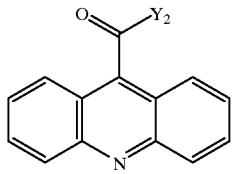

(VII)

wherein $Y_2$ represents an eliminative group, to obtain a compound represented by the following formula (VIII):

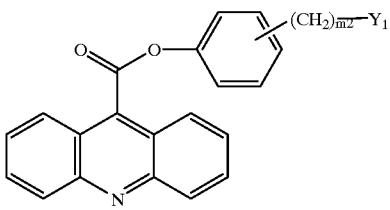

(VIII)

wherein $Y_1$ and m2 have the same meanings as defined above; and then reacting the thus-obtained compound with a polyamine, which is represented by the following formula (IX):

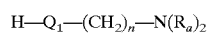

(IX)

wherein $Q_1$ and n have the same meanings as defined above and $R_a$ is each independently a hydrogen atom or an amino-protecting group and which contains a primary amino group at an end thereof, said primary amino group being optionally protected by one or two protecting groups, and a primary or secondary amino group at an opposite end thereof, in the presence of an appropriate base to obtain a 9-acridine ester represented by the following formula (X):

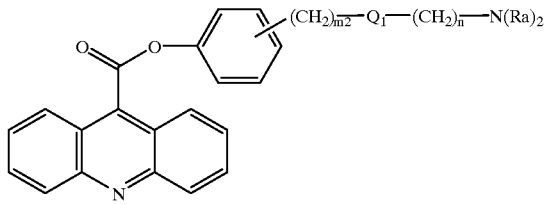

(X)

wherein $Q_1$, $R_a$, m2 and n have the same meanings as defined above; and when the one or two protecting groups of the terminal primary amino group exist, eliminating the one or two protecting groups; and then causing maleic anhydride to act.

9. A process for the preparation of an acridine compound represented by the following formula (IIb"):

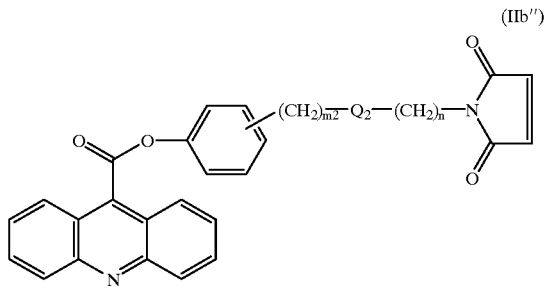

wherein $Q_2$ represents a group —S— or a group —O(CH$_2$CH$_2$O)$_l$— (l: a number of 1 to 3), m2 denotes a number of 0 to 2, and n stands for a number of 1 to 2, which comprises reacting a phenol derivative, which is represented by the following formula (XI):

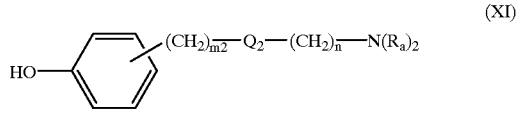

wherein $Q_2$, m2 and n have the same meanings as defined above and $R_a$ is each independently a hydrogen atom or an amino-protecting group and which has a thioether or polyether structure having at an end thereof a primary amino group protected by one or two protecting groups, with a 9-acridinecarboxylic acid derivative, which is represented by the following formula (VII):

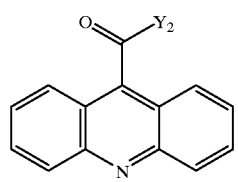

wherein $Y_2$ represents an eliminative group, to obtain an acridine ester represented by the following formula (XII):

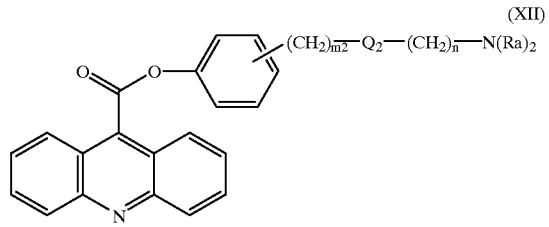

wherein $Q_2$, $R_a$, m2 and n have the same meanings as defined above; and subsequent to deprotection of the terminal amino group, causing maleic anhydride to act.

10. A labeling method of an analyte, which comprises reacting an acridine compound, which is represented by the following formula (I):

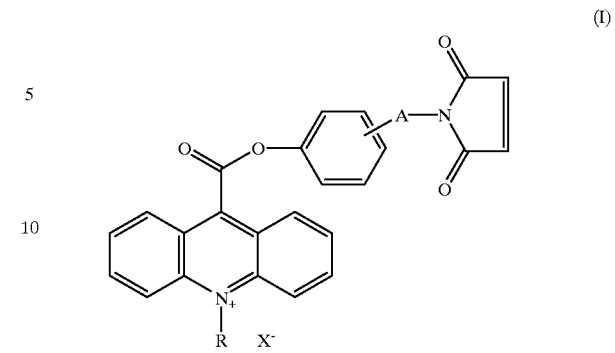

wherein
A represents the following group:

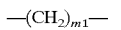

or

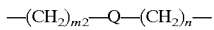

in which Q represents a group —S$^+$RX$^-$—; a group —N$^+$RR$_1$X$^-$— wherein R$_1$ represents an alkyl group having 1 to 6 carbon atoms or an aryl group; a group

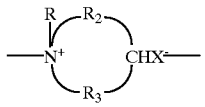

wherein R$_2$ and R$_3$ may be the same or different and are each independently a group —(CH$_2$)$_k$— (k; a number of 1 to 3); or —O(CH$_2$CH$_2$O)$_l$— (l: a number of 1 to 3), m1 stands for a number of 1 to 6,
m2 denotes a number of 0 to 2,
n means a number of 1 to 2;
R represents an alkyl group having 1 to 6 carbon atoms or an aryl group; and
X$^-$ represents an anion, with SH groups in said analyte.

11. A prelabeling method of an analyte, which comprises reacting an acridine compound represented by the following formula (II):

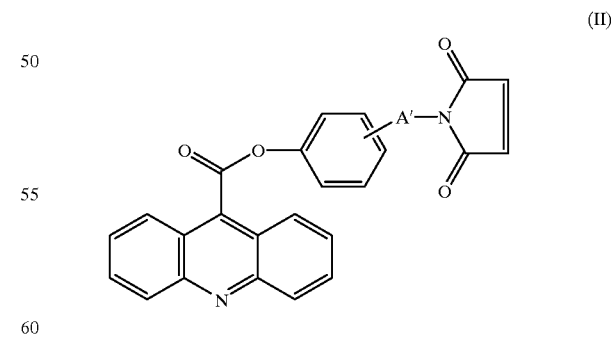

wherein
A' represents the following group:

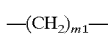

or

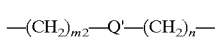

in which Q' represents a group —S—; a group —NR$_1$— wherein R$_1$ represents an alkyl group having 1 to 6 carbon atoms; a group

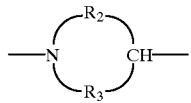

wherein R$_2$ and R$_3$ may be the same or different and are each independently a group —(CH$_2$)$_k$— (k: a number of 1 to 3); or —O(CH$_2$CH$_2$O)$_l$— (l: a number of 1 to 3); and m1, m2 and n have the same meanings as defined in claim 1, with SH groups in said analyte.

12. The SH-labeling reagent of claim 1 wherein A is —(CH$_2$)$_{m2}$—Q—(CH$_2$)$_n$—.

13. The SH-labeling reagent of claim 2 wherein A' is —(CH$_2$)$_{m2}$—Q'—(CH$_2$)$_n$—.

14. The labeling method of claim 10 wherein A is —(CH$_2$)$_{m2}$—Q—(CH$_2$)$_n$—.

15. The prelabeling method of claim 11 wherein A' is —(CH$_2$)$_{m2}$—Q'—(CH$_2$)$_n$—.

\* \* \* \* \*